United States Patent
Haik

(10) Patent No.: US 10,184,937 B2
(45) Date of Patent: Jan. 22, 2019

(54) MINIMALLY INVASIVE ASSESSMENT OF IGE MEDIATED ALLERGY

(75) Inventor: Yousef Haik, Greensboro, NC (US)

(73) Assignees: United Arab Emirates University, Al Ain (AE); University Of North Carolina At Greensboro, Greensboro, NC (US)

( * ) Notice: Subject to any disclaimer, the term of this patent is extended or adjusted under 35 U.S.C. 154(b) by 858 days.

(21) Appl. No.: 12/751,574

(22) Filed: Mar. 31, 2010

(65) Prior Publication Data

US 2011/0059550 A1    Mar. 10, 2011

Related U.S. Application Data

(60) Provisional application No. 61/164,912, filed on Mar. 31, 2009.

(51) Int. Cl.
*G01N 33/68* (2006.01)
*G01N 33/543* (2006.01)

(52) U.S. Cl.
CPC ... *G01N 33/54346* (2013.01); *G01N 33/6893* (2013.01); *G01N 2800/24* (2013.01)

(58) Field of Classification Search
CPC ......... G01N 33/54346; G01N 33/6893; G01N 2800/24
USPC ................................................ 436/526, 518
See application file for complete search history.

(56) References Cited

U.S. PATENT DOCUMENTS

| | | | | |
|---|---|---|---|---|
| 5,597,531 A | * | 1/1997 | Liberti et al. | 422/401 |
| 5,789,261 A | * | 8/1998 | Schwartz | G01N 33/54393 435/288.3 |
| 6,494,921 B1 | * | 12/2002 | Bennett | D06F 35/00 8/137 |
| 2003/0146529 A1 | | 8/2003 | Chen | |
| 2003/0202980 A1 | | 10/2003 | Caplan et al. | |
| 2005/0042685 A1 | * | 2/2005 | Albert et al. | 435/7.2 |
| 2005/0266433 A1 | * | 12/2005 | Kapur | G01N 33/54326 435/6.11 |
| 2006/0177855 A1 | | 8/2006 | Utermohlen et al. | |
| 2007/0224225 A1 | | 9/2007 | Garreta et al. | |
| 2008/0182339 A1 | * | 7/2008 | Jung et al. | 436/174 |

OTHER PUBLICATIONS

Gause, "ELISA Protocols" Uniformed Services University, Bethesda, MD Feb. 5, 2004.*
Lu et al. (Journal of Controlled Release, vol. 137, 2009, pp. 54-62).*
Steitz et al. (Journal of Magnetism and Magnetic Materilas, vol. 311, 2007, pp. 300-305).*
Chatterjee et al., "Size dependent magnetic properties of iron oxide nanoparticles", Journal of Magnetism and Magnetic Materials 257 (2003) 113-118.

* cited by examiner

*Primary Examiner* — Lisa V Cook
(74) *Attorney, Agent, or Firm* — Akerman LLP; Michael K. Dixon

(57) ABSTRACT

A system and method for determining the presence and level of allergy indicators in a human fluid sample such as, but not limited to, blood serum and saliva, is disclosed. In another embodiment, the method may assess a level of allergens in a consumable product. The system and method may make use of functionalized magnetic nanoparticles that have modified surfaces suitable for attracting allergy indicators from human fluid sample and allergens from consumable products. The system and method may provide a minimally invasive assessment of allergy indicators to determine whether one is allergic to a substance.

12 Claims, 9 Drawing Sheets

MINIMALLY INVASIVE ASSESSMENT OF IGE MEDIATED ALLERGY

CROSS-REFERENCE TO RELATED APPLICATION

This patent application claims priority to U.S. Provisional Patent Application No. 61/164,912, filed Mar. 31, 2009, which is incorporated by reference in its entirety.

FIELD OF THE INVENTION

This invention relates to a system for assessing the presence and level of allergy indicators in human fluid samples and of allergens in consumable products.

BACKGROUND OF THE INVENTION

Allergy is a major cause of illness in the United States, effecting millions of Americans and compromising their daily life. The most current information on the prevalence of food allergy in the U.S. indicates that up to 6% of children and 4% adults of the total population have IgE mediated food allergies. Severe food related allergic reactions result in an estimated 30,000 emergency room visits, 2,000 hospitalizations and 150 deaths annually. Furthermore, clinical data and surveys have observed an increase in the prevalence of allergies, including food allergies, over the years.

The most severe and life threatening adverse reactions to foods are associated with immunoglobulin E (IgE)—mediated hypersensitivity. An allergic reaction occurs due to an abnormal immune system response to specific antigens or proteins present in food. The clinical manifestations of food allergies range from mild irritations to life threatening respiratory distress and shock. Symptoms often occur within a few minutes to hours after consumption of the allergen present in food and generally progresses on a continuum from a mild reaction to a severe reaction.

Currently there are three major approaches being used in the diagnosis of allergies, including: 1) Skin test or skin prick test (SPT), 2) Assays of serum IgE, levels and 3) Histamine release test. The major drawbacks of these tests is that these tests may result in false negative or false positive results, have low sensitivity, and are highly invasive. Additionally, these tests must be administered by trained personnel in controlled environments, which results in a considerable cost increase. The CAP allergy evaluation technology must be administered by trained personnel, thereby incurring substantial costs and take a substantial amount of time before rendering test results. Hence, there is an urgent need to develop reliable assays to detect the onset of food allergies in a rapid, sensitive and less invasive way that does not involve highly trained personnel and expensive equipment, making the assay cost effective.

SUMMARY OF THE INVENTION

This invention relates to a system and method for determining the presence and level of allergy indicators in a human fluid sample such as, but not limited to, blood serum and saliva. In another embodiment, the method may assess a level of allergens in a consumable product. The system and method makes use of functionalized magnetic nanoparticles that have modified surfaces suitable for attracting allergy indicators from human fluid sample and allergens from consumable products. The system and method provides a minimally invasive assessment of allergy indicators to determine whether one is allergic to a substance.

The system for determining the presence of one or more allergy indicators in a human fluid may include one or more magnetic particles configured to capture allergy indicators. In one embodiment, the magnetic particles may be uncovered and may include a charge to attract the allergy indicators. In another embodiment, the magnetic particle may be coated with a coating that allows for the capture of allergy indicators in at least one human fluid. The coating may be a surface charge that is opposite to a surface charge of the allergy indicator. In another embodiment, the coating may be comprised of a charged polymer having a surface charge that is opposite to a surface charge of one or more allergy indicators. In yet another embodiment, the coating may be an IgE specific allergen to capture specific IgEs from a human fluid. In another embodiment, the coating may be an IgG to capture a specific allergen from a consumable product.

The magnetic particle of the system and method may be one or more nanoparticles. The nanoparticles may have a size between about 5 nm and about 100 nm. The nanoparticle may include a plurality of nanoparticles. Once the magnetic particles have favorable surface properties, as previously described, such as containing a charge of have been coated with a coating that allows for the capture of allergy indicators in at least one human fluid, the magnetic particles may be coated with an allergen.

The method for determining the presence of an allergy indicator in a fluid may include providing one or more magnetic particles with a favorable surface property, which may include a favorable charge. In one embodiment, the magnetic particles may include a coating that allows for the capture of the allergy indicator in the fluid, coating the magnetic particle with an allergen and coating the one or more magnetic particles with the allergy indicator by placing the magnetic particles into the fluid where the magnetic particle attracts the allergy indicator. The method may also include removing the magnetic particle from the fluid after a period of time, exposing the magnetic particle to an anti-allergy indicator in a solution to separate the allergy indicator from the magnetic particle, and analyzing the solution to determine absorbance of the solution.

The step of providing the magnetic particles with a coating that allows for the capture of the allergy indicator in the fluid, further comprises synthesizing magnetic particles by a chemical method that reduces chemical slats to nanoparticles of at least one substance. The step may also include sonicating the solution, peptizing the synthesized magnetic particles with an acid, washing the magnetic particles, filtering the magnetic particles, and drying the magnetic particles.

The step of enhancing the surface properties of the magnetic nanoparticles may include washing with acidic or basic media to expose the particles' surface charges.

The step of coating the one or more magnetic particles with an allergen may include coating the at least one magnetic particle with a positively charge polymer.

The step of coating the magnetic particle with the allergy indicator by placing the magnetic particle into the fluid where magnetic particle attracts the allergy indicator may include coating the magnetic particle with a peanut extract.

The step of removing the magnetic particle from the fluid after a period of time may include removing magnetic particle with a permanent magnet.

The step of removing the magnetic particle from the fluid after a period of time may include removing the magnetic particle from the fluid after about two hours.

The step of exposing the magnetic particle to an anti-allergy indicator in a solution to separate the allergy indicator from the magnetic particle may include exposing the magnetic particle to an anti-allergy indicator for between about five minutes and about one hour.

The step of analyzing the solution to determine absorbance of the solution may include reading the absorbance at 405 nm in a plate reader.

The step of removing the magnetic particle from the fluid after a period of time may include removing the at least one magnetic particle with a permanent magnet.

These and other embodiments are described in more detail below.

BRIEF DESCRIPTION OF THE FIGURES

The accompanying drawings, which are incorporated in and form a part of the specification, illustrate embodiments of the presently disclosed invention and, together with the description, disclose the principles of the invention.

DETAILED DESCRIPTION OF THE INVENTION

As shown in FIGS. 1-10, this invention is directed to a system and method for detecting the presence of allergy indicators in human fluids and consumable products. In one embodiment, an assay using nanotechnology as a platform to detect the presence of allergy indicators in human fluids and consumable products may be used. Magnetic nanoparticles may be synthesized using chemical methods with size range between 5-100 nm. The size of particles is not limiting the advantage of the detection method, however it complements the effectiveness of the detection method. The smaller the particles, with reasonable magnetic moment level the higher the effectiveness of allergy indicators from both human fluid sample and consumable products.

The magnetic nanoparticles may then be functionalized with a suitable coating element that allows for the capture of the allergy indicators in human fluids and consumable products. In one embodiment, the magnetic nanoparticles themselves may possess a surface charge that is opposite to that of the allergy indicator, hence allowing the capturing of the allergy indicators from the heterogeneous sample solution.

In another embodiment, the magnetic nanoparticles may be coated with a charged polymer or ligand that has a surface charge opposite to that of the allergy indicator.

In another embodiment, the magnetic nanoparticles may be coated with IgE specific allergen to capture specific IgEs from human solution. The magnetic nanoparticles may alternatively be coated with IgG to capture specific allergen from a consumable product.

A magnetic immunoassay may be utilized to quantify the concentration of captured allergy indicators. In the magnetic immunoassay, a secondary marker may be utilized to quantify the concentration of the allergy indicator. The magnetic assay developed using nanoparticles that were functionalized with allergen extract was successful in detecting specific IgE in plasma as well as saliva. Additionally, when the sensitivity of the magnetic assay was compared to that of a traditional ELISA, the magnetic assay was found to be nearly twice as sensitive. Moreover, this degree of sensitivity was achieved by using only 100 µg of nanoparticles and 50 µl of plasma.

Figure 8:
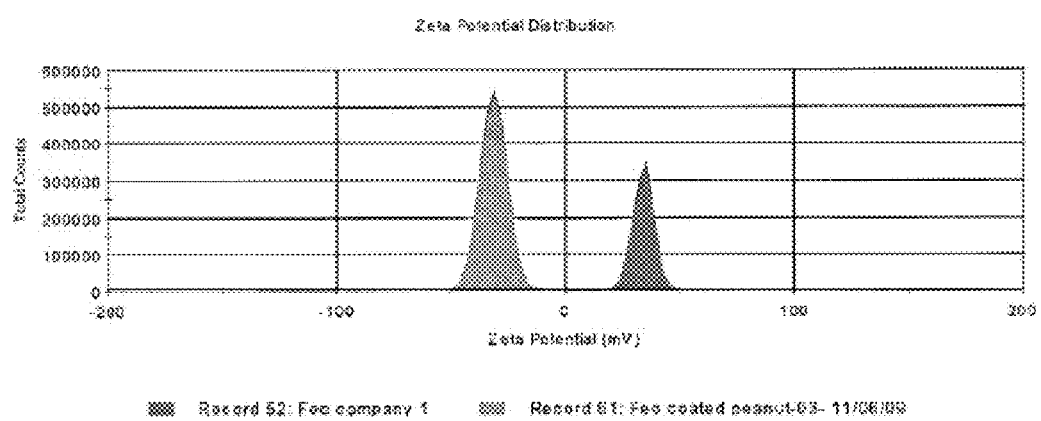
FIG. 8 is a graph showing the zeta potential distribution. SEM was used to measure the size of the particles, and zeta was used to measure the change in the surface charge.
Figure 9:
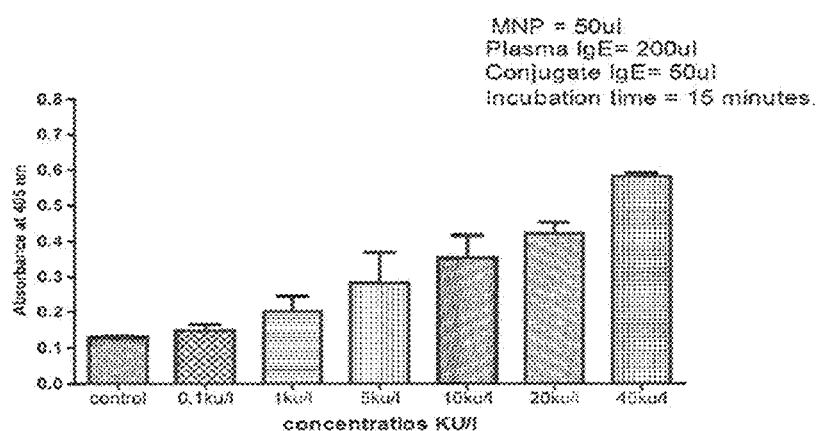
FIG. 9 shows a graph demonstrating the sensitivity of the assay through a plasma diluted with a known amount of IgE concentration to a very low limit. The assay was able to detect at concentrations as low as 0.1 ku/l.
Figure 10:
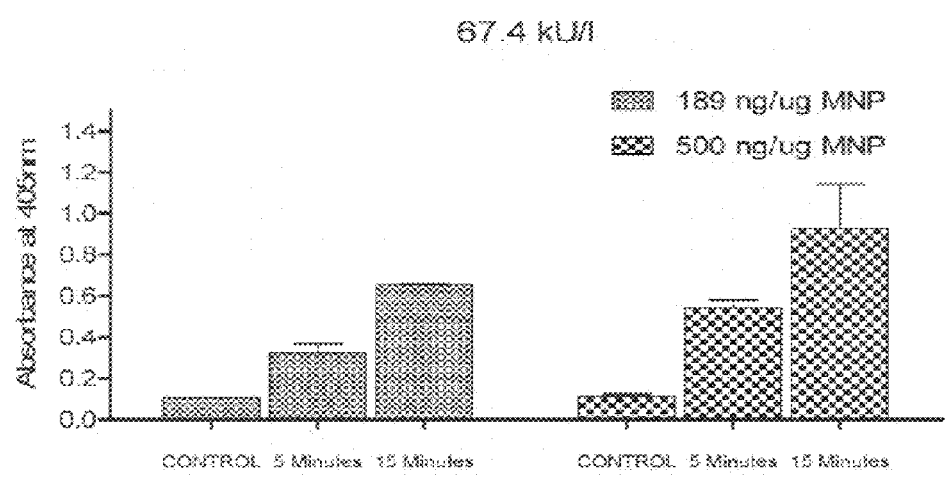
FIG. 10 is a graph that shows that the assay works at five minutes of incubation as well as at 15 minutes of incubation.

In one embodiment, the system may be directed to use of a single antibody in the magnetic ELISA. Such system is possible because the magnetic particles are covered with an allergen. The coating of the allergens is demonstrated in FIGS. 8-10. FIG. 8 shows the zeta potential distribution. SEM was used to measure the size of the particles, and zeta was used to measure the change in the surface charge. FIG. 9 demonstrates the sensitivity of the assay through a plasma diluted with a known amount of IgE concentration to a very low limit. The assay was able to detect IgE at concentrations as low as 0.1 ku/l. FIG. 10 shows that the assay works at five minutes of incubation as well as at 15 minutes of incubation.

Example 1

In one embodiment, iron oxide nanoparticles were synthesized in three main steps as described below and in Chatterjee J, Haik Y and Chen C J. Size dependent magnetic properties of iron oxide nanoparticles (2003). J Magn. Magn. Mater., 257:113-118). Briefly, ferrous chloride and ferric chloride were co-precipitated by sodium hydroxide. The mixture of ferrous chloride and ferric chloride were then mixed in a molar ratio of 1:2 in deionized water at a concentration of 0.1 M iron ions. Next, a highly concentrated solution of sodium hydroxide (10 M) was added, and the solution was stirred continuously for the ions to be co-precipitated. The solution with the precipitates was stirred in a high speed for about one hour at 20° C. and subsequently heated to 90° C. for about one hour with stirring. The iron oxide dispersion was then sonicated for about ten minutes at 50% amplitude using an Ultrasonic homogenizer. Next, the ultrafine magnetic particles obtained were peptized by nitric acid (2 M). The precipitate was washed repeatedly with deionized water, filtered, and dried in vacuum to obtain fine iron oxide particles. The particle size distribution was tested using a transmission electron microscopy and was found to be $9^{\pm}2.5$ rim. The charge of the particles was measured using a Zetasizer (Malvern Instruments, UK) and was found to be anionic.

The particles produced were functionalized by coating them with a positively charged polymer, polyethylenimine (PEI). The charge on the coated particles was verified by measuring zeta potential with the Zetasizer, nano series (Malvern, UK). The zeta potential of coated nanoparticles was found to be 6.04 mV. The positively coated particles were then coated with whole peanut extract by incubating the particles and extract in a 1:1 ratio for about three hours at 37° C. The coated panicles were then magnetically separated from the peanut extract using a permanent magnet. The supernatant was collected, and the particles left behind were washed five times with phosphate buffered saline (PBS), pH 7.4. After the last wash, the particles were suspended in PBS to create the needed concentration of nanoparticles/ml of PBS.

The coating on the particles was verified by three independent methods. First, the zeta potential of the particles was measured before and after coating with the peanut protein. The zeta potential changed from (6.04 mV) on the peanut uncoated particles to a negative potential (−10.12 mV) after coating with the peanut extract. Second, the protein concentration of the peanut extract was determined. In one embodiment, the protein concentration was determined using a Bicinchoninic acid (BSA) kit supplied by Pierce, Thermo Scientific, IL, before and after the particles were coated with peanut extract. A decrease in protein concentration of the peanut extract after the nanoparticles were coated was observed. The initial protein concentration of the extract was 4.88 µg/µl, however, after coating the nanoparticles, the protein concentration of the extract decreased to 2.79 µg/µl. These data suggest that the difference in protein concentration was the amount coated onto the nanoparticles. Third, the protein concentration of the coated and uncoated particles was determined by BSA assay. The protein concentration of the coated particles was found to be 254 ng/µg of particle as compared to 13 ng/µg of particle for the uncoated particles. Taken together, these results strongly indicated that the nanoparticles were successful coated with the peanut extract.

Experiments were carried out in microfuge tubes that had been blocked with protein free blocking buffer T-20 solution supplied by Pierce, Thermo Scientific, IL. Briefly, different concentrations ranging from 0 µg to 400 µg of the functionalized particles were incubated with the appropriate volume of plasma from an allergic individual for two hours. The volume was previously optimized to facilitate the capture of peanut specific IgE. Excess substrate was washed with phosphate buffered saline and tween-20 (PBST) and the particles along with the captured IgEs were isolated with a permanent magnet. The particles were then incubated with an anti-human IgE that was conjugated to alkaline phosphatase, which was available from Sigma, Mo. This incubation was carried out for about one hour. This time period had also been previously optimized. The excess anti-human IgE was washed away with three PBST washes. Alkaline phosphate substrate solution, 1-step pNPP (paranitrophenol-phosphate), which was available from Thermo Scientific, IL, was added, and the tubes were incubated in the dark. After about 15 minutes of incubation, the nanoparticles were pulled aside with a permanent magnet and about 100 ml of the solution was delivered into a 96-well plate via a pipet. For each sample in every experiment carried out, appropriate controls were run.

Figure 1:
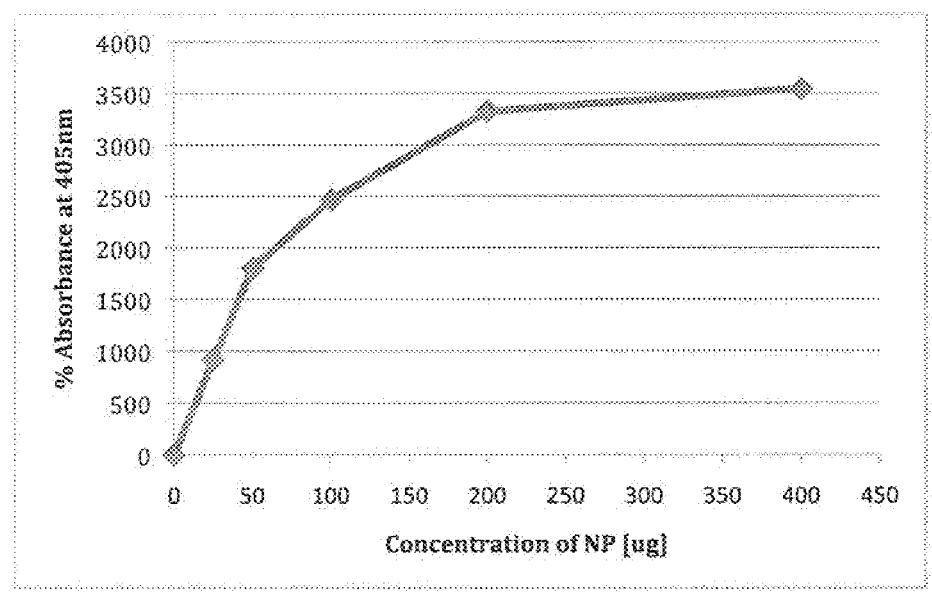
FIG. 1 is a graph that shows different concentrations of functionalized nanoparticles that were incubated with a fixed volume of plasma from an allergic individual. The assay was carried out as described in the results section. The absorbance obtained was plotted relative to the concentration of the particles. As seen in the figure above, the absorbance first increased with increasing concentration of the particles from 25 µg to 200 µg and then stabilized at 400 µg.
Figure 2:
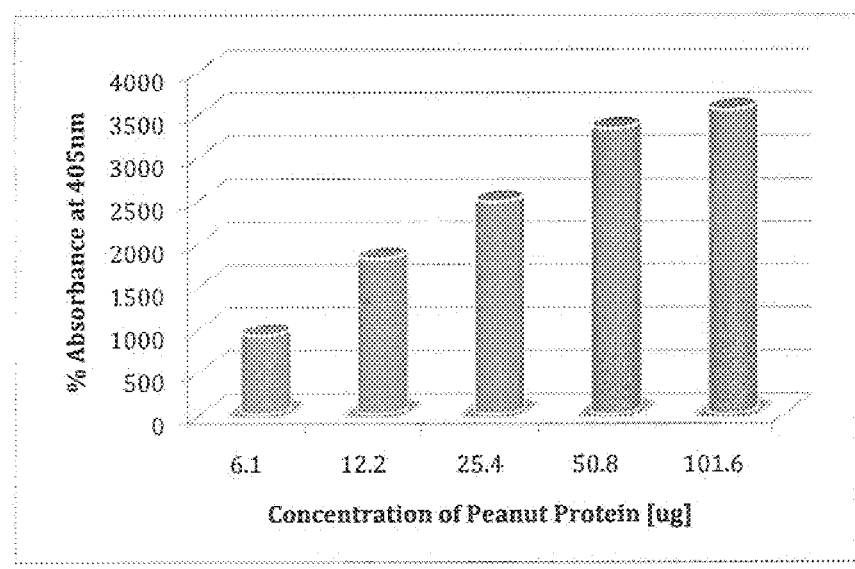
FIG. 2 is a graph that shows different amounts of the peanut allergen coated on the functionalized nanoparticles that were incubated with allergic plasma. The obtained absorbance was plotted on the graph relative to the peanut protein concentration on the coated particles. The data demonstrated that 6 µg of peanut extract was sufficient to detect the presence of peanut specific IgE in plasma.

The absorbance of the solution was read at 405 nm in a BIO-tek microtiter plate reader, which was available from BIO-tek powerwave XS, VT. FIG. 1 shows that 25 µg of functionalized nanoparticles was sufficient to detect the presence of peanut specific IgE in plasma. Additionally, a dose-dependent increase in absorbance as the amount of functionalized particles increased from 0 to 200 µg and at a higher amount (400 µg), it was observed that the absorbance started to saturate. Since 100 µg of functionalized particles fell in the linear part of the absorbance curve, this amount of functionalized particles was used for further experiments.

Particles corresponding with different amounts of peanut protein were incubated with a fixed amount of plasma from an allergic individual as described above and absorbance obtained was plotted relative to the amount of peanut protein coated on the particles. The results depicted in FIG. 2 demonstrate that 6 µg of peanut protein coated onto the particles was sufficient to detect peanut specific IgE in the given volume of plasma. Additionally, the results show that with increasing amounts of the peanut protein there was an increase in the ability to the assay to detect peanut specific IgE. However, the increases leveled off at 50.8 µg and higher concentrations, suggesting saturation in the ability of the functionalized particles to detect peanut specific IgE present in the given volume of plasma.

Figure 3:
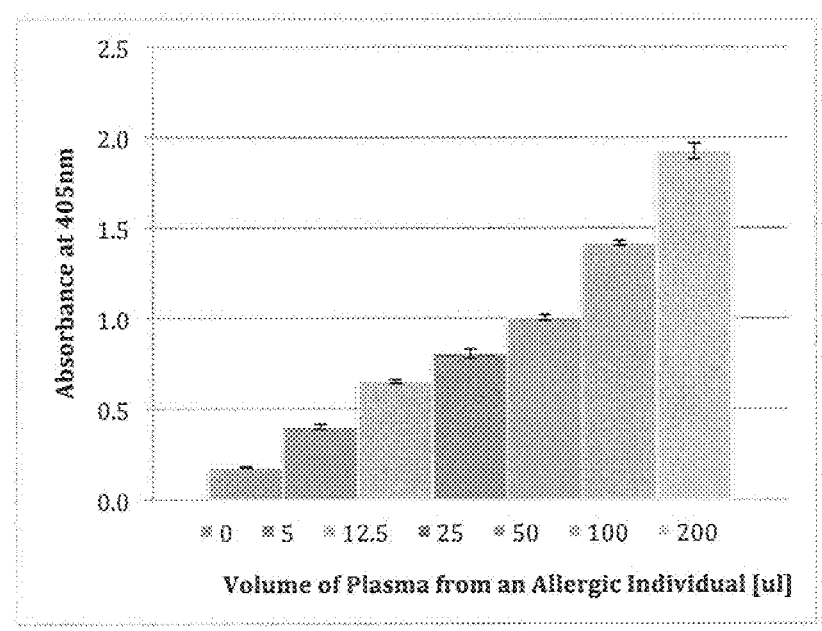
FIG. 3 is a graph that shows 100 µg of functionalized nanoparticles were incubated with increasing volume of plasma, ranging from 0 to 200 µg, in duplicates. The absorbance detected was plotted against the volume of plasma used for each condition. As can be seen in the graph above, using as little as 50 µg of plasma was sufficient to detect significant differences between the samples and the control (0 µl of plasma) by 450%.
Figure 4:
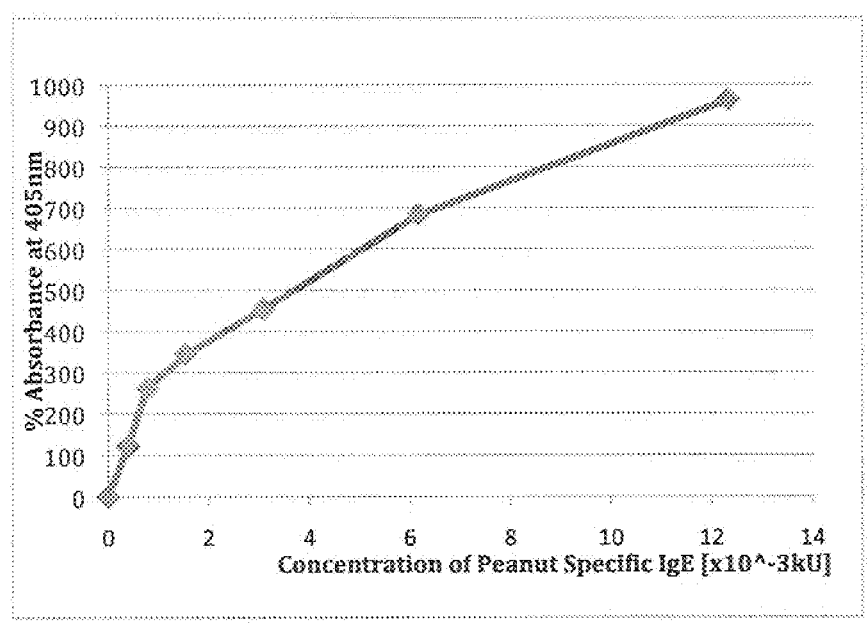
FIG. 4 is a graph that shows 100 µg of functionalized nanoparticles were incubated with increasing concentration of peanut specific IgEs, ranging from $0.385 \times 10^{-3}$ kU to $12.32 \times 10^{-3}$ kU. The absorbance obtained was plotted relative to the concentration of IgEs incubated. As can be seen in FIG. 4, the assay had the ability to detect IgE as low as $0.385 \times 10^{-3}$ kU by 100% as compared to the negative control.

A fixed amount (100 µg) of functionalized nanoparticles were incubated with different volumes of plasma from the allergic individual. These experiments were done according to the protocol described above, and the absorbance obtained was plotted for each volume of plasma. As shown in FIG. 3, the data indicated a dose-dependent increase in absorbance as the volume of plasma increased from 0 to 200 µl. Moreover, 50 µl of plasma was sufficient to detect significant differences between the particles incubated in the absence or presence of plasma by 450%. For experiments henceforth, 50 µl of plasma was used to further optimize the assay. The amount of peanut specific IgE present in the allergic individuals plasma was determined by an immuno CAP assay and found to be approximately 61.5 kU/L. Using this as a reference value, the approximate amount of peanut specific IgE present in plasma was calculated for the different volumes incubated with 100 μg of functionalized particles. These data, depicted in FIG. 4, clearly indicated that the assay had the ability to detect peanut specific IgE as low as $0.385 \times 10^{-3}$ kU/L by 100% as compared to the negative control sample that did not have any IgE.

Figure 5:
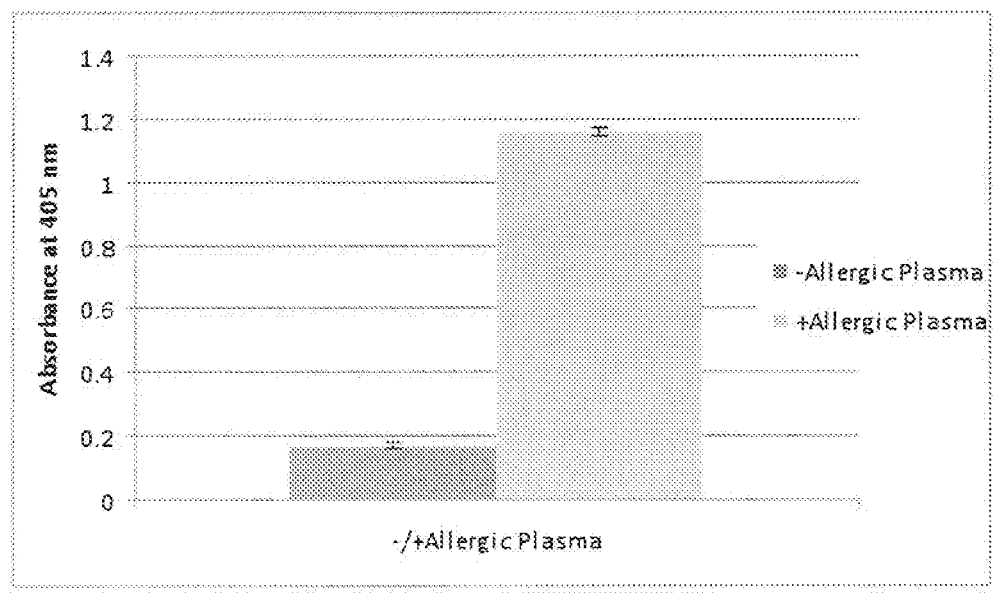
FIG. 5 is a graph that shows the specificity of the nanoparticles was determined by incubating functionalized particles with peanut extract in the absence or presence of allergic plasma. As can be seen in FIG. 5, the absorbance of the samples incubated in the presence of peanut specific IgE was found to be approximately 600% more specific as compared to the sample that was incubated in the absence of plasma. The data above is the average of three distinct experiments.

An amount of functionalized particles, such as 100 μg, was incubated either in the absence or presence of 50 μl of plasma from the allergic individual. This experiment was repeated in triplicate, and the average absorbances obtained together with the standard deviation are shown in FIG. 5. The absorbance in presence of allergic plasma was 600% times more than the absorbance in the absence of allergic plasma. This data demonstrated that the absorbance obtained from the samples incubated with allergic plasma was not due to the non-specific binding on anti-human IgE to the functionalized particles, and demonstrated that the signal is extremely specific for peanut IgE present in plasma.

The same amount of peanut extract was coated in each well of the ELISA plate and 100 μg of functionalized nanoparticles. The appropriate wells of the ELISA and tubes for the nano assay were incubated with or without the allergic plasma. The samples without allergic plasma were considered to be negative controls for both of the ELISA and the assay with the nanoparticles. These experiments were carried out in triplicate, following the determined protocol for both methods. The data obtained from these experiments clearly shows that the nano assay has more than twice the sensitivity as compared to the ELISA shown in FIG. 5. Thus, the magnetic assay was found to have high sensitivity and specificity for the detection of peanut specific IgE in plasma.

In order to determine the sensitivity of the assay, plasma sample was diluted to 0.1 kU/L. Peanut extract coated magnetic nanoparticles were added to the plasma solutions. The particles were incubated for 15 minutes. As FIG. 9 shows, the assay was able to detect up to 0.1 kU/L.

To assess the rapidity by which a test can be performed, plasma sample of 67.4 kU/L was incubated for 5 and 15 minutes. FIG. 10 shows that the assay is able to selectively detect allergens even after only five minutes incubation.

Example 2

In another embodiment, the system and method maybe used to determine whether a person is allergic to latex. Latex is a natural milky sap of the rubber tree (*Hevea brasiliensis*) that coagulates on exposure to air. This sap is used to make natural rubber, which is found in thousands of industrial products in the U.S., and, more importantly, nearly 400 of these products are used in the medical community including gloves, catheters, facemask, mattresses, stethoscope, blood tourniquets, rubber syringe stoppers, and medical vial stoppers. These commercial products are composed of two types of substances that have the potential to cause medical problems, including: 1) the chemical substances like antioxidants that are added at the time of processing latex and manufacturing the product, and 2) the natural proteins found in latex that are associated with immunoglobulin E (IgE) mediated reactions.

Latex proteins found in natural rubber can elicit two types of allergic reactions. The first is a delayed-type contact dermatitis (type IV dermatitis), that is limited to the skin wherein rash appears 12-36 hours after contact with a latex product. Type IV dermatitis is a T-cell dependent reaction caused by chemicals used in latex production. Additionally, the natural latex proteins cause a more serious IgE antibody-mediated allergic reaction (type I), which occurs in people who have previously been exposed to latex and have become sensitized. The hypersensitive reaction is due to the immune response that activates mast cells and basophils and causes the release of histamine, leukotrienes and prostaglandins. An allergic individual may experience symptoms such as itching, redness, swelling, sneezing, and wheezing. Occasionally, a patient may experience severe allergic reaction called anaphylaxis, which is characterized by symptoms such as shock, severe trouble breathing or loss of blood pressure and, if not immediately treated, death.

Concentrations of 400, 200, 100, 50, 25 and 0 of functionalized nanoparticles particles were obtained by serial dilutions. Additionally, a negative control was also run that contained 200 μg. These functionalized nanoparticles were then incubated with latex specific IgE obtained from PlasmaLab international, Everett, Wash. Next, the excess unbound IgEs were washed away, and the magnetic nanoparticles were resuspended in appropriate volume. The nanoparticles were then incubated with Anti-human IgE (Sigma, St Louis, Mo.). Nanoparticles and anti-human IgE were incubated for few minutes. After incubation, the unbound anti-IgE was washed away.

Figure 6:
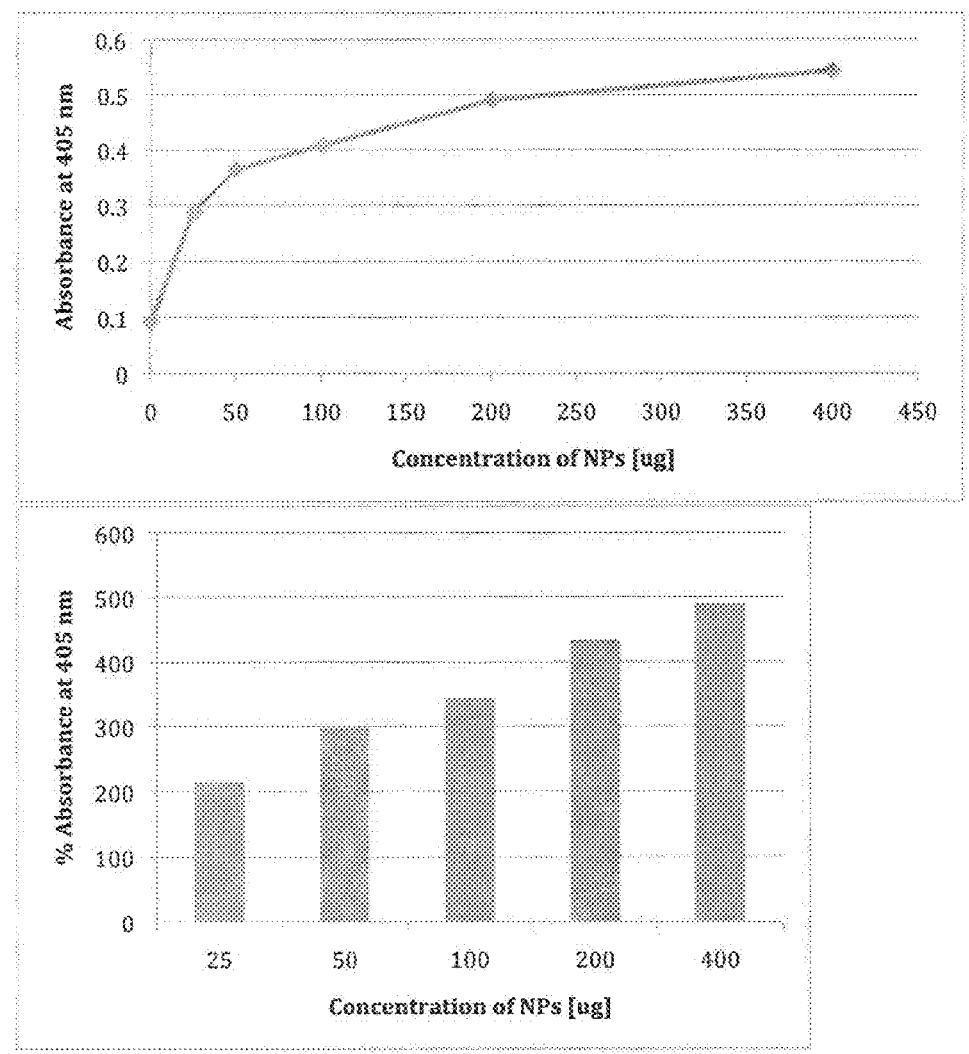
FIG. 6 is a collection of graphs that show diagnostic measurement for latex allergy at different NPs concentration.
Figure 7:
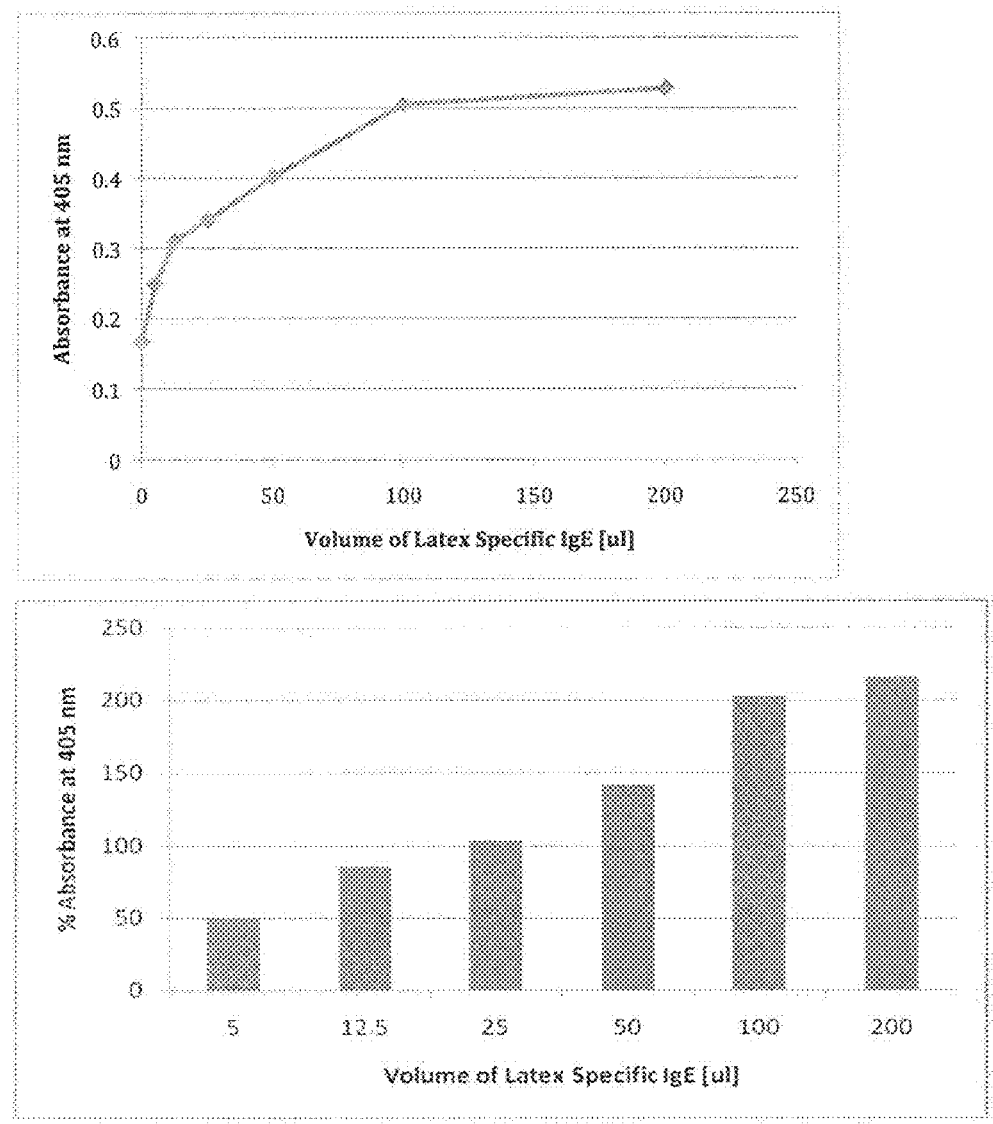
FIG. 7 is a collection of graphs that show diagnostics at different IgE volumes.

Results from these experiments are shown in FIGS. 6 and 7. FIG. 6 shows the results obtained for different concentrations of latex-functionalized nanoparticles in which 50 micro grams of IgEs were added to the solution. FIG. 6 shows that the functionalized nanoparticles are able to detect all IgEs in the sample. FIG. 6 also shows the relative measurement obtained of the IgEs compared to a negative control. Even at low concentrations, the signal is 200% higher than that of the control. FIG. 7 shows the results obtained in optimizing the volume/concentration of IgE that can be detected by 100 μg of functionalized magnetic nanoparticles. The results clearly indicate a high sensitivity for the detection method even at low concentrations. It is noticeable in both graphs that at 100 μg of functionalized nanoparticles and 50 μl of IgEs produce the same detection results and indication of reproducibility of the results with higher amounts of functionalized nanoparticles and IgEs.

The foregoing is provided for purposes of illustrating, explaining, and describing embodiments of this invention. Modifications and adaptations to these embodiments will be apparent to those skilled in the art and may be made without departing from the scope or spirit of this invention.

I claim:

1. A method for determining a presence of an allergy indicator in a fluid, comprising:
    providing at least one magnetic particle with a coating that allows for the capture of the allergy indicator in the fluid;
    coating the at least one magnetic particle with an allergen;
    coating the at least one magnetic particle with the allergy indicator by placing the at least one magnetic particle into the fluid where the at least one magnetic particle attracts the allergy indicator;
    removing the at least one magnetic particle from the fluid after a period of time;
    exposing the at least one magnetic particle to an anti-allergy indicator in a solution to separate the allergy indicator from the at least one magnetic particle;
    analyzing the solution to determine absorbance of the solution to determine the presence of the allergy indicator; and
    wherein coating the at least one magnetic particle with an allergen comprises coating the at least one magnetic particle with a charged polymer having a surface charge that is opposite to a surface charge of the at least one allergy indicator.

2. The method of claim 1, wherein providing the at least one magnetic particle with a coating that allows for the capture of the allergy indicator in the fluid, further comprises synthesizing iron oxide particles.

3. The method of claim 2, wherein providing the at least one magnetic particle with a coating that allows for the capture of the allergy indicator in the fluid, further comprises synthesizing magnetic particles by a chemical method that reduces chemical salts to nanoparticles of at least one substance.

4. The method of claim 3, wherein providing the at least one magnetic particle with a coating that allows for the capture of the allergy indicator in the fluid, further comprises sonicating the solution, peptizing the magnetic particles with an acid, washing the magnetic particles, filtering the magnetic particles, and drying the magnetic particles.

5. The method of claim 1, wherein coating the at least one magnetic particle with an allergen comprises coating the at least one magnetic particle with a positively charge polymer.

6. The method of claim 1, wherein coating the at least one magnetic particle with the allergy indicator by placing the at least one magnetic particle into the fluid where the at least one magnetic particle attracts the allergy indicator comprises coating the at least one magnetic particle with a peanut extract.

7. The method of claim 1, wherein removing the at least one magnetic particle from the fluid after a period of time comprises removing the at least one magnetic particle with a magnet.

8. The method of claim 1, wherein removing the at least one magnetic particle from the fluid after a period of time comprises removing the at least one magnetic particle from the fluid after about two hours.

9. The method of claim 1, wherein exposing the at least one magnetic particle to an anti-allergy indicator in a solution to separate the allergy indicator from the at least one magnetic particle comprises exposing the at least one magnetic particle to an anti-allergy indicator for between about five minutes and about one hour.

10. The method of claim 1, wherein analyzing the solution to determine absorbance of the solution comprises reading the absorbance at 405 nm in a plate reader.

11. The method of claim 1, wherein removing the at least at least one magnetic particle from the fluid after a period of time comprises removing the at least one magnetic particle with a magnet.

12. The method of claim 1, wherein enhancing surface properties of the at least one magnetic particle comprises washing with acidic or basic media to expose surface charges on the at least one magnetic particle.

* * * * *